US00PP11185P

United States Patent [19]

Nijenhuis et al.

[11] Patent Number: Plant 11,185

[45] Date of Patent: Jan. 25, 2000

[54] FLORIBUNDA ROSE PLANT NAMED 'KORFLEUR'

[75] Inventors: Johannes Wilhelmus Maria Nijenhuis, Bemmel; Hette Spek, Boskoop, both of Netherlands

[73] Assignee: Bear Creek Gardens, Inc., Medford, Oreg.

[21] Appl. No.: 09/107,060

[22] Filed: Jun. 30, 1998

[51] Int. Cl.[7] ..... A01H 5/00

[52] U.S. Cl. ..... Plt./151

[58] Field of Search ..... Plt./150, 151, 108

*Primary Examiner*—Howard J. Locker

*Attorney, Agent, or Firm*—Klarquist Sparkman Campbell Leigh & Whinston LLP

[57] ABSTRACT

Floribunda rose plant having red flowers, very high cut-flower production, and very long vase life.

1 Drawing Sheet

The present invention relates to a new and distinct variety of rose plant of the floribunda class which was originated by me by discovering a single branch spontaneous mutation on a rose plant of the variety KORflapei (U.S. Plant Pat. No. 6,695) growing in a greenhouse in Bemmel, The Netherlands, which bore a red flower as compared to the bright yellow flowers of KORflapei having yellow anthers.

'KORfleur' differs from KORflapei in flower color and in anther (filament) color. It has the same high cut flower production and long vase life of its parent KORflapei.

Asexual reproduction of this new variety by budding, as performed at Boskoop, The Netherlands, and Somis, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage: Spontaneous mutant of KORflapei (U.S. Plant Pat. No. 6,695).

Classification:

*Botanical.*—Rosa hybrida.

*Commercial.*—Floribunda.

FLOWER

Observations made from specimens grown in a greenhouse environment at Boskoop, The Netherlands, and Somis, Calif. from February 1997 to June 1998.

Blooming habit: Continuous.

Bud:

*Size.*—About 1¼ inches long when the petals start to unfurl.

*Form.*—Long, pointed ovoid.

*Color.*—When sepals first divide, but color is near Red Group 53B. When half blown, the upper sides of the petals are near Red Group 53A, and the lower sides of the petals are near Red Group 53B.

*Sepals.*—Color: Green Group 138B. Surface texture: Covered in fine hairs. There are three normally to heavily appendaged sepals. There are two unappendaged sepals with hairy edges.

*Receptacles.*—Color: Green Group 138B. Shape: Funnel. Size: Small (about ¼"×5/16"). Surface: Smooth.

*Peduncle.*—Length: Medium, averaging about 3 inches. Surface: Smooth. Color: Green Group 137C. Strength: Stiff, erect, heavy.

Bloom:

*Size.*—Medium to small. Average open diameter is about 3½ inches.

*Borne.*—Singly or sometimes several together in clusters of three to five blooms having a rounded shape.

*Stems.*—Strong, averaging about 16–22 inches in length.

*Form.*—When first open: High centered. Permanence: Retains its form to the end, all petals curl, quill fashion.

*Petalage.*—Number of petals under normal conditions: 30 .

*Color.*—The upper sides of the petals are Red Group 53A. The reverse sides of the petals are Red Group 53B. The base of the petals has no color spot on the outer surface. The inner surface has a color spot about 3/16×3/16" in Red Group 53A. On either side of this darker area are two light patches, about ⅓"×⅓". They are close to Yellow Group 4C with Red Group 53B overlaid on top. The major color on the upper sides is Red Group 53A.

*Variegations.*—Occasional greenish-white streaks on the guard petals.

*Discoloration.*—At the end of the first day: No change. At the end of the third day: No change. No change through day 14 in the vase.

*Fragrance.*—None.

Petals:

*Texture.*—Thick.

*Shape.*—Round.

*Form.*—Heavily quilled.

*Arrangement.*—Imbricated. Petaloids in the center: None.

*Persistence.*—Petals drop off cleanly before drying.

*Lastingness.*—On the plant: Very long (*10 days*). As a cut flower: Very long (*14 days*).

Reproductive parts:

*Anthers.*—Size: Medium. Quantity: Many. Color: Red Group 46A. Arrangement Regular around styles.

*Filaments.*—Color: Red Group 46A.

*Pollen.*—Color: Gold yellow.

*Styles.*—Color: Red Group 46A.

*Stigmas.*—Color: Greenish-white.

Plant:

*Form:* Bush.

*Growth:* Vigorous; upright; branching. At maturity, after one year in the greenhouse, height is six feet, width is three and one half feet.

Foliage: Number of leaflets on normal mid-stem leaves: Five.

*Size.*—Medium (5½×4½ inches).

*Quantity.*—Abundant.

*Color.*—New foliage: Upper side and lower sides: Greyed-Orange Group 176D, turning to green very quickly. Old foliage: Upper side: Yellow-Green Group 147A. Lower side: Yellow-Green Group 147C.

Leaflets:

*Shape.*—Pointed oval.

*Texture.*—Smooth.

*Edge.*—Serrated.

*Serration.*—Single.

*Petiole rachis.*—Color: Reddish.

*Petiole underside.*—Smooth, with occasional prickles.

*Stipules.*—Medium (5/16"), edged with a few glands.

*Disease resistance.*—Susceptible to mildrew under normal growing conditions in a greenhouse at Somis, Calif. Not tested for resistance to blackspot and rust.

Wood:

*New wood.*—Color: Reddish, turning green very quickly. Bark: Smooth.

*Old wood.*—Color: Green Group 137C. Bark: Smooth.

Prickles:

*Quantity.*—On main canes from base: Few. On laterals from main canes: Few.

*Form.*—Medium, hooked slightly downward.

*Color when young*—Greyed-Purple Group 183C.

*Color when mature*—Brown.

Small prickles:

*Quantity.*—On main stalks: None. On laterals: None.

We claim:

1. A new and distinct variety of rose plant of the floribunda class, as herein shown and described, characterized particulary by its red flower color, high cut-flower production, and long vase life.

* * * * *

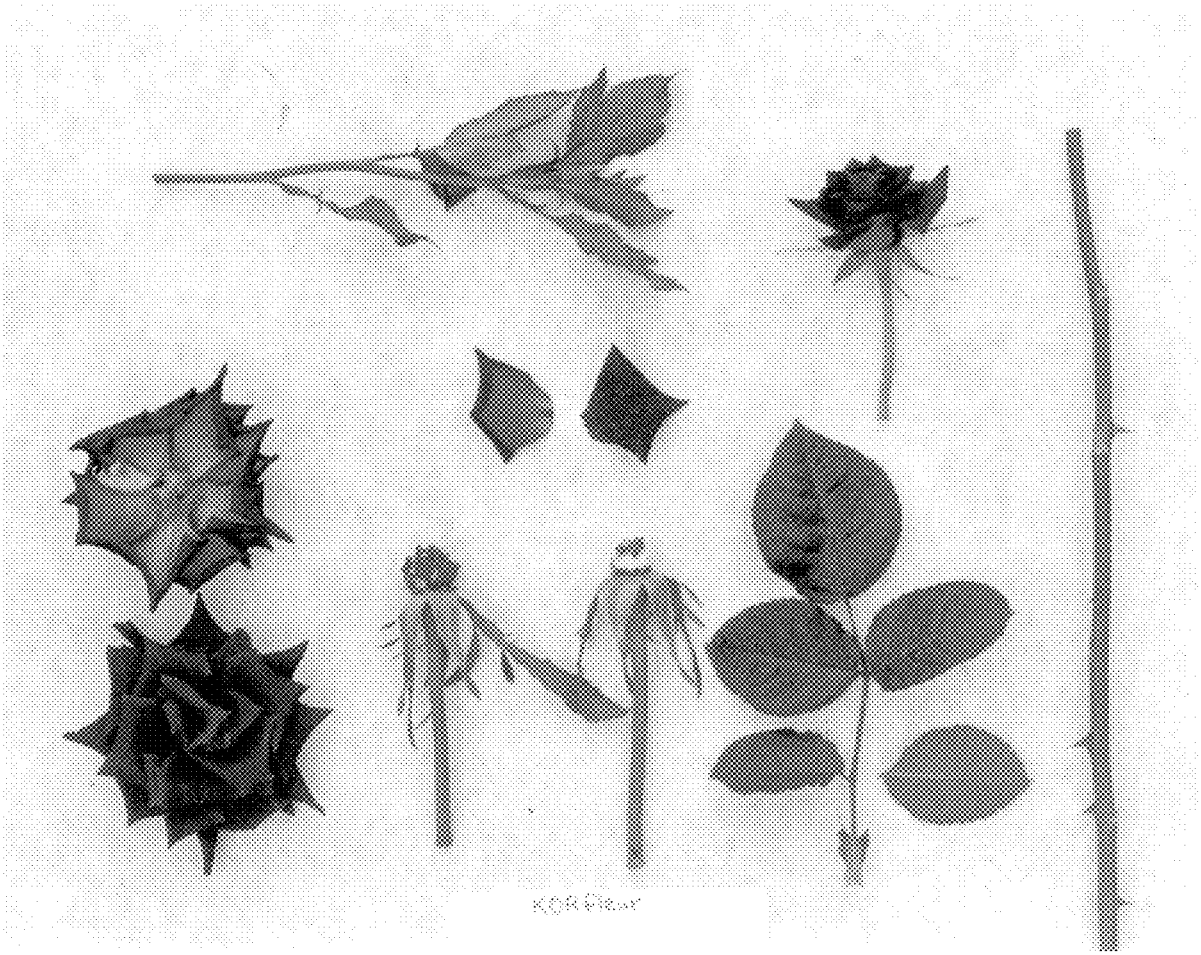

UNITED STATES PATENT AND TRADEMARK OFFICE

CERTIFICATE OF CORRECTION

PATENT NO. : PP11,185
DATED : January 25, 2000
INVENTOR(S) : Johannes Wilhelmus , Marie Nijenhuis and Hette Spek It is certified that error appears in the above-identified patent and that said Letters Patent is hereby corrected as shown below:

In the Specification:

Column 1,
Line 40, reads "1¼ inches". It should read --1 — 1¼ inches--.
Line 43, reads "but color". It should read --bud color--.

Column 2,
Line 8, reads "3 ½ inches". It should read --3 –3½ inches--.
Line 44, reads "Arrangement Regular". It should read --Arangement: Regular--.

Signed and Sealed this

Third Day of July, 2001

Nicholas P. Godici

*Attest:*

*Attesting Officer*

NICHOLAS P. GODICI
*Acting Director of the United States Patent and Trademark Office*